US00PP36682P2

(12) United States Plant Patent
van den Hoogen

(10) Patent No.: US PP36,682 P2
(45) Date of Patent: May 13, 2025

(54) *HYPERICUM* PLANT NAMED 'ALLHYBELL'

(50) Latin Name: ***Hypericum androseamum* L.**
Varietal Denomination: ALLHYBELL

(71) Applicant: Wilhelmus T. J. van den Hoogen, Cuijk (NL)

(72) Inventor: Wilhelmus T. J. van den Hoogen, Cuijk (NL)

(73) Assignee: ALLPLANTS HOLDING B.V., Cuijk (NL)

( * ) Notice: Subject to any disclaimer, the term of this patent is extended or adjusted under 35 U.S.C. 154(b) by 0 days.

(21) Appl. No.: 18/931,751

(22) Filed: Oct. 30, 2024

(51) Int. Cl.
*A01H 5/02* (2018.01)
*A01H 6/00* (2018.01)

(52) U.S. Cl.
USPC ..... Plt./442

(58) Field of Classification Search
USPC ..... Plt./263.1, 442
See application file for complete search history.

(56) References Cited

U.S. PATENT DOCUMENTS

PP19,324 P2 * 10/2008 Hooijman ..... A01H 5/02
Plt./226

* cited by examiner

*Primary Examiner* — Karen M Redden
(74) *Attorney, Agent, or Firm* — C. Anne Whealy

(57) ABSTRACT

A new and distinct cultivar of *Hypericum* plant named 'ALLHYBELL', characterized by its broadly upright plant habit; moderately vigorous growth habit; moderately strong to strong stems; dark green-colored leaves; freely flowering habit and high fruit density; spherical and glossy greenish yellow-colored fruits; and suitability as a cut flower plant.

3 Drawing Sheets

Figure 1:
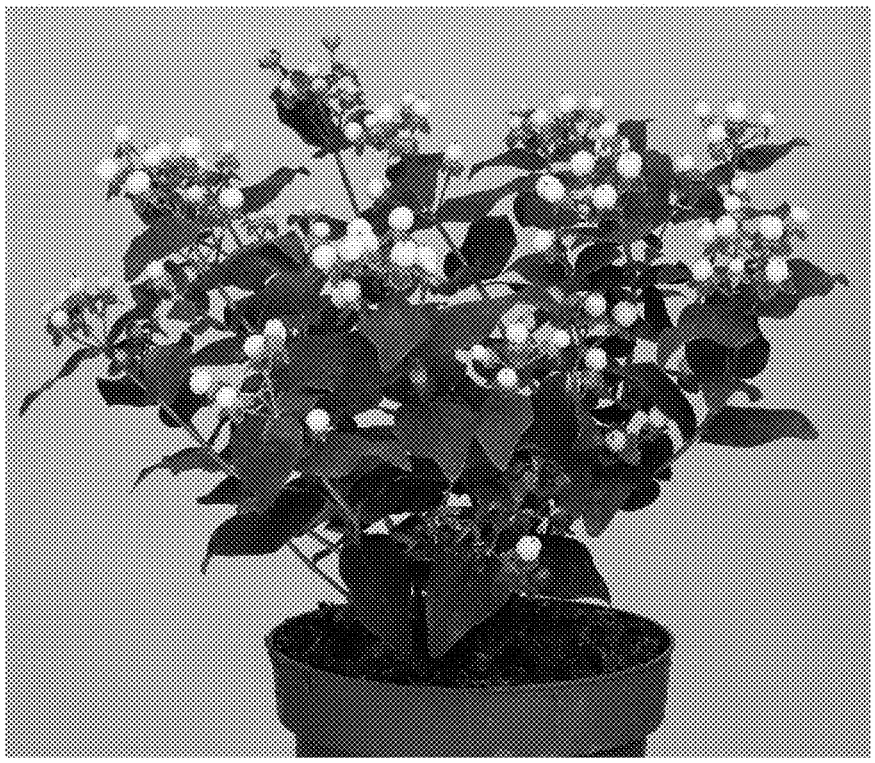

Botanical designation: *Hypericum androseamum* L.
Cultivar denomination: 'ALLHYBELL'.

CROSS-REFERENCE TO CLOSELY-RELATED APPLICATIONS

A European Community Plant Breeder's Rights application for the instant plant was filed by the Assignee, Allplants Holding B.V. of Cuijk, The Netherlands on Apr. 3, 2024, application number 2024/0792. Foreign priority is not claimed to this application.

BACKGROUND OF THE INVENTION

The present invention relates to a new and distinct cultivar of *Hypericum* plant, botanically known as *Hypericum androseamum* L., typically grown as cut flowers and hereinafter referred to by the name 'ALLHYBELL'.

The new *Hypericum* plant is a product of a planned breeding program conducted by the Inventor in Cuijk, The Netherlands. The objective of the breeding program is to create new *Hypericum* plants with numerous attractive fruits.

The new *Hypericum* plant originated from an open-pollination in September 2015 in Cuijk, The Netherlands of a proprietary selection of *Hypericum androseamum* L. identified as code number 2-2012-23-1, not patented, as the female, or seed parent with an unknown proprietary selection of *Hypericum androseamum* L. as the male, or pollen, parent. The new *Hypericum* plant was discovered and selected by the Inventor as a single flowering plant from within the progeny of the stated open-pollination in a controlled outdoor nursery environment in Cuijk, The Netherlands in August 2016.

Asexual reproduction of the new *Hypericum* plant by vegetative cuttings in a controlled outdoor nursery environment in Cuijk, The Netherlands since August 2016 has shown that the unique features of this new *Hypericum* plant are stable and reproduced true to type in successive generations.

SUMMARY OF THE INVENTION

Plants of the new *Hypericum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'ALLHYBELL'. These characteristics in combination distinguish 'ALLHYBELL' as a new and distinct *Hypericum* plant:

1. Broadly upright plant habit.
2. Moderately vigorous growth habit.
3. Moderately strong to strong stems.
4. Dark green-colored leaves.
5. Freely flowering habit and high fruit density.
6. Spherical and glossy greenish yellow-colored fruits.
7. Suitable as a cut flower plant.

Plants of the new *Hypericum* differ primarily from plants of the female parent selection in fruit texture and shape as plants of the new *Hypericum* produce glossy spherical fruits whereas fruits of plants of the female parent selection are dull in luster and elliptical in shape.

Plants of the new *Hypericum* can be compared to plants of the *Hypericum hybrida* 'Allhy1236', disclosed in U.S. Plant Pat. No. 28,134. In side-by-side comparisons plants of the new *Hypericum* differ primarily from plants of 'Allhy1236' in the following characteristics:

1. Plants of the new *Hypericum* produce fewer fruits per plant than plants of 'Allhy1236'.
2. Plants of the new *Hypericum* produce greenish yellow-colored fruits whereas fruits of plants of 'Allhy1236' are white in color.
3. Fruits of plants of the new *Hypericum* are more rounded in shape than fruits of plants of 'Allhy1236'.

BRIEF DESCRIPTION OF THE PHOTOGRAPHS

The accompanying colored photographs illustrate the overall appearance of the new *Hypericum* plant showing the colors as true as it is reasonably possible to obtain in colored reproductions of this type. Colors in the photographs may differ slightly from the color values cited in the detailed botanical description which accurately describe the actual colors of the new *Hypericum* plant.

The photograph on the first sheet (FIG. 1) is a side perspective view of a typical fruiting plant of 'ALLHYBELL' grown in a container.

Figure 2:
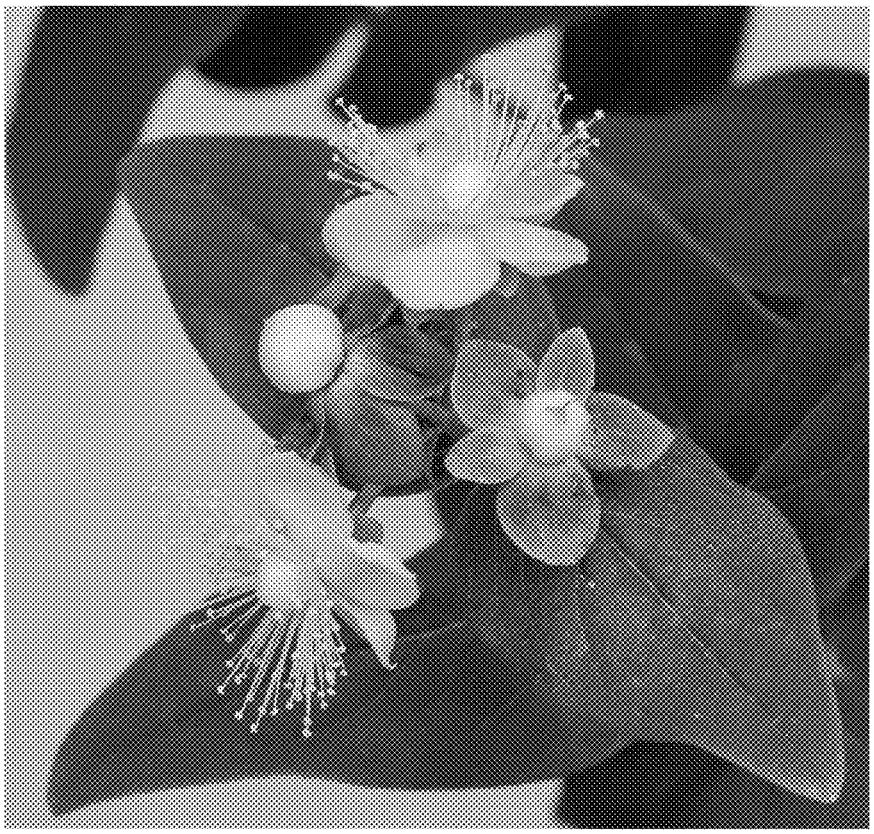

The photograph on the second sheet (FIG. 2) is a close-up view of a typical flowering plant of 'ALLHYBELL' with developing fruits.

Figure 3:
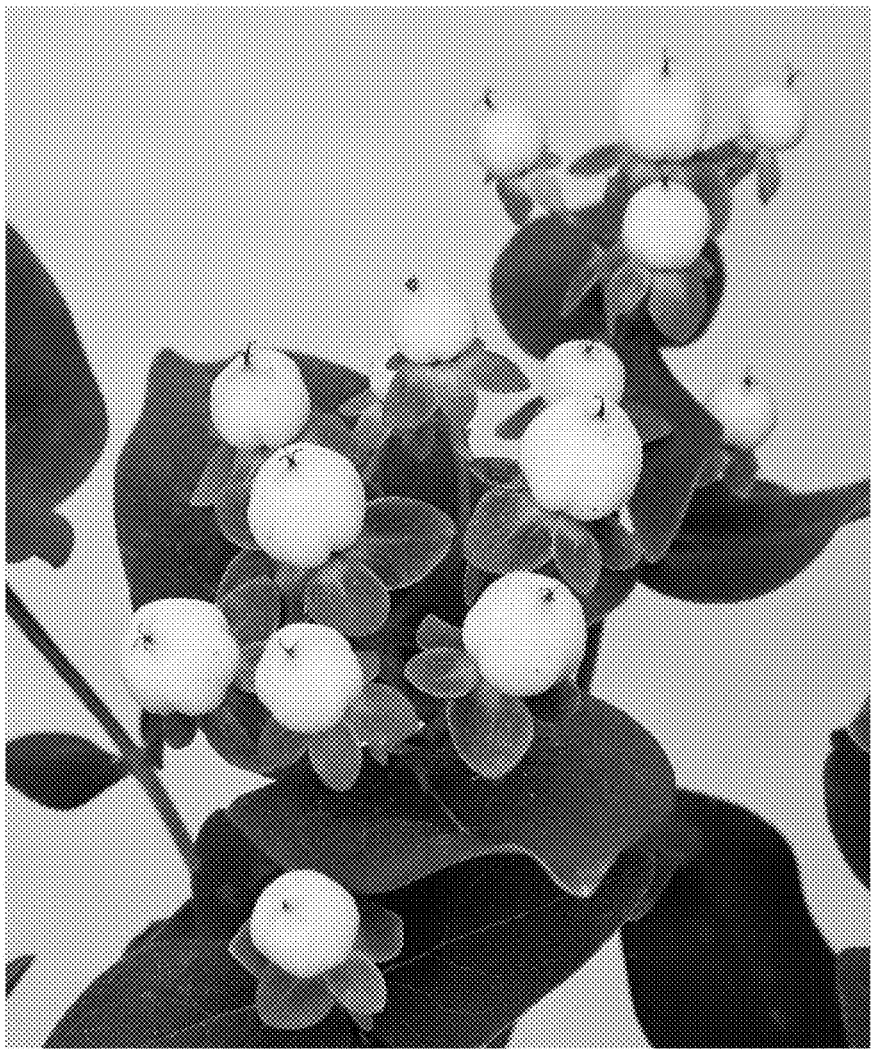

The photograph on the third sheet (FIG. 3) is a close-up view of a typical fruiting plant of 'ALLHYBELL'.

DETAILED BOTANICAL DESCRIPTION

Plants used for the aforementioned photographs and following description were grown during the autumn in 25-cm containers and in ground beds in an outdoor nursery in Cuijk, The Netherlands and under cultural practices typical of commercial cut flower *Hypericum* production. During the production of the plants, day temperatures ranged from 23° C. to 28° C. and night temperatures ranged from 7° C. to 12° C. Plants were pinched one time and were six months old when the photographs and description were taken. In the following description, color references are made to The Royal Horticultural Society Colour Chart, Sixth Edition, except where general terms of ordinary dictionary significance are used.

Botanical classification: *Hypericum androseamum* L. 'ALLHYBELL'.

Parentage:

*Female, or seed, parent*.—Proprietary selection of *Hypericum androseamum* L. identified as code number 2-2012-23-1, not patented.

*Male, or pollen, parent*.—Unknown proprietary selection of *Hypericum androseamum* L., not patented.

Propagation:

*Type cutting*.—Vegetative cuttings.

*Time to initiate roots, summer*.—About three weeks at temperatures ranging from 12° C. to 30° C.

*Time to produce a rooted young plant, summer*.—About 24 to 32 days at temperatures ranging from 12° C. to 30° C.

*Root description*.—Fine, fleshy; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Perennial shrub, typically grown as a cut flower; broadly upright plant habit; overall plant shape, broad inverted triangle; moderately vigorous growth habit and moderate growth rate.

*Branching habit*.—When pinched, about five basal branches develop per plant each with about three secondary laterals.

*Plant height*.—About 42.1 cm.

*Plant width* (*spread*).—About 42.3 cm.

*Lateral branch description*.—Length: About 24.6 cm. Diameter: About 3.5 mm. Internode length: About 4.2 cm. Strength: Moderately strong to strong. Texture and luster: Smooth, glabrous; slightly glossy. Color, developing: Close to 146B. Color, fully developed: Close to 200B to 200D.

Leaf description:

*Arrangement*.—Opposite, simple; sessile; about twelve leaves (six pairs) develop per lateral branch.

*Length*.—About 7.3 cm.

*Width*.—About 4.7 cm.

*Shape*.—Ovate.

*Apex*.—Mostly obtuse to minutely retuse.

*Base*.—Truncate.

*Margin*.—Entire.

*Texture and luster, upper surface*.—Smooth, glabrous; slightly glossy.

*Texture and luster, lower surface*.—Slightly rugose, glabrous; matte.

*Venation pattern*.—Pinnate.

*Color*.—Developing leaves, upper surface: Close to a blend of 144A and 146A. Developing leaves, lower surface: Close to 146B. Fully expanded leaves, upper surface: Close to N189A; venation, close to N144A. Fully expanded leaves, lower surface: Close to 147B; venation, close to 146C and 146D.

Flower description:

*Flower type, arrangement and flowering habit*.—Single rotate flowers arranged in terminal and axillary compound cymes; freely flowering habit with about nine flowers per cyme and about 13 flowers per lateral branch; flowers face mostly upright to outwardly.

*Fragrance*.—None detected.

*Natural flowering season*.—Plants flower continuously from mid-summer to late summer in The Netherlands.

*Flower longevity*.—Depending on temperature, open flowers last about three days on the plant; flowers not persistent; fruits fully ripen in about 25 days.

*Fruit longevity* (*postproduction*).—About 30 days.

*Flower buds*.—Length: About 1.1 cm. Diameter: About 1.1 cm. Shape: Orbicular. Color: Immature sepals, close to 138B and immature petals, close to 12A and 12B.

*Inflorescence height*.—About 6 cm.

*Inflorescence diameter*.—About 7 cm.

*Flower diameter*.—About 2.6 cm.

*Flower depth* (*height*).—About 1.9 cm.

*Petals*.—Quantity and arrangement: Five in a single whorl. Length: About 1.3 cm. Width: About 1.2 cm. Shape: Broadly elliptic to roughly orbicular; concave; horizontal to slightly reflexed. Apex: Broadly acute. Base: Attenuate. Margin: Entire. Texture and luster, upper surface: Smooth, glabrous; matte to slightly glossy. Texture and luster, lower surface: Smooth, glabrous; moderately glossy. Color: When opening and fully opened, upper surface: Close to 14B; color does not change with subsequent development. When opening and fully opened, lower surface: Close to 12B; towards the margins and apex, closer to 14B; color does not change with subsequent development.

*Sepals*.—Quantity and arrangement: Five in a single whorl. Length: About 9.5 mm. Width: About 7 mm. Shape: Ovate to broadly ovate; slightly to moderately reflexed. Apex: Acute to broadly acute. Base: Broadly cuneate. Margin: Entire. Texture and luster, upper and lower surfaces: Smooth, glabrous; matte. Color: When opening, upper surface: Close to a blend of 141B and 143A. When opening, lower surface: Close to 138B. Fully opened, upper surface: Close to 143A. Fully opened, lower surface: Close to a blend of 138A and 138B.

*Peduncles*.—Length: About 2.2 cm. Diameter: About 2 mm. Texture: Smooth, glabrous. Strength: Moderately strong. Aspect: Main peduncles, erect; lateral peduncles, about 45° from stem axis. Color: Close to 146D.

*Pedicels*.—Length: About 1.5 cm. Diameter: About 1.5 mm. Texture: Smooth, glabrous. Strength: Moderately strong. Aspect: Main pedicels, erect; lateral pedicels, about 40° from peduncle axis. Color: Close to 144A and 144B.

*Reproductive organs*.—Stamens: Quantity per flower: About 90.Filament length: About 1.3 cm. Filament color: Close to 14B. Anther length: About 0.75 mm. Anther shape: Broadly oval; dorsifixed. Anther color: Close to 15A. Pollen amount: Moderate. Pollen color: Close to 11D. Pistils: Quantity per flower: Single pistil with three stigmas. Pistil length: About 3.5 mm. Stigma shape: Club-shaped. Stigma color: Close to 54C. Style length: About 3.25 mm. Style color: Close to 150C. Ovary color: Close to 151D.

*Fruits*.—Quantity per lateral branch: About 13. Length: About 1.3 cm Diameter: About 1.3 cm. Shape: Spherical. Texture and luster: Smooth, glabrous; glossy. Color: Close to 160C; proximally, close to 150D.

*Seeds*.—Quantity per fruit: More than 100. Length: About 0.9 mm. Diameter: About 0.5 mm. Color: Close to 200A.

Pathogen & pest resistance: To date, plants of the new *Hypericum* have not been observed to be resistant to pathogens and pests common to *Hypericum* plants.

Temperature tolerance: Plants of the new *Hypericum* have been observed to tolerate high temperatures about 30° C. and to be hardy to USDA Hardiness Zone 7.

It is claimed:

1. A new and distinct *Hypericum* plant named 'ALLHYBELL' as herein illustrated and described.

* * * * *